US010524800B2

(12) United States Patent
Roselli

(10) Patent No.: US 10,524,800 B2
(45) Date of Patent: Jan. 7, 2020

(54) METHOD AND APPARATUS FOR SUBSTANTIALLY BLOCKING BLOODFLOW THROUGH A DISSECTED AORTA

(71) Applicant: THE CLEVELAND CLINIC FOUNDATION, Cleveland, OH (US)

(72) Inventor: Eric E. Roselli, Rocky River, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 113 days.

(21) Appl. No.: 15/593,717

(22) Filed: May 12, 2017

(65) Prior Publication Data
US 2017/0333046 A1   Nov. 23, 2017

Related U.S. Application Data

(60) Provisional application No. 62/337,373, filed on May 17, 2016.

(51) Int. Cl.
*A61B 17/12* (2006.01)
*A61F 2/07* (2013.01)
*A61B 17/00* (2006.01)

(52) U.S. Cl.
CPC .. *A61B 17/12109* (2013.01); *A61B 17/12036* (2013.01); *A61B 17/12136* (2013.01);
(Continued)

(58) Field of Classification Search
CPC .......... A61B 17/1214; A61B 17/12109; A61B 17/12022; A61B 17/12031;
(Continued)

(56) References Cited

U.S. PATENT DOCUMENTS 5,507,767 A    4/1996  Maeda et al.
6,361,545 B1 *  3/2002  Macoviak ........ A61B 17/12109
                                                        606/151
(Continued)

FOREIGN PATENT DOCUMENTS

EP    2363075 A1    7/2011

OTHER PUBLICATIONS

Search Report and Written Opinion for corresponding PCT/US2017/032377, dated Jul. 18, 2017, pp. 1-15.
(Continued)

*Primary Examiner* — Katherine M Shi
*Assistant Examiner* — Brigid K Byrd
(74) *Attorney, Agent, or Firm* — Tarolli, Sundheim, Covell & Tummino LLP

(57) ABSTRACT

An implantable expandable device includes an occluding surface oriented substantially in a transverse plane. The occluding surface is bounded by a lateral occluding surface edge and a medial occluding surface edge. The occluding surface has an occluding surface body located transversely between the lateral and medial occluding surface edges. A supporting structure is located entirely inferiorly to the occluding surface. The supporting surface includes a plurality of struts extending substantially in the superior-inferior direction. At least a first one of the struts is a full-height strut and spans substantially a full superior-inferior height of the device. At least a second one of the struts is a reduced-height strut and spans substantially less than a full superior-inferior height of the device. The occluding surface substantially occludes a transverse cross-section of the false lumen to substantially block bloodflow in the superior-inferior direction within the false lumen.

21 Claims, 14 Drawing Sheets

(52) U.S. Cl.
CPC ...... *A61F 2/07* (2013.01); *A61B 2017/00867* (2013.01); *A61B 2017/00893* (2013.01); *A61F 2210/0014* (2013.01)

(58) Field of Classification Search
CPC ....... A61B 17/12122; A61B 17/12131–12195; A61B 17/0057; A61B 2017/00592; A61B 2017/00597; A61B 2017/00601
See application file for complete search history.

(56) References Cited

U.S. PATENT DOCUMENTS

| | | | |
|---|---|---|---|
| 6,368,338 B1 | 4/2002 | Konya et al. | |
| 6,428,558 B1 | 8/2002 | Jones et al. | |
| 7,799,072 B2 | 9/2010 | Greenberg | |
| 8,911,468 B2 | 12/2014 | Ogle et al. | |
| 2004/0044391 A1 | 3/2004 | Porter | |
| 2006/0052804 A1* | 3/2006 | Mialhe | A61B 17/0057 606/157 |
| 2006/0058833 A1 | 3/2006 | VanCamp et al. | |
| 2007/0265656 A1 | 11/2007 | Amplatz et al. | |
| 2009/0062844 A1* | 3/2009 | Tekulve | A61B 17/0057 606/213 |
| 2010/0030259 A1* | 2/2010 | Pavcnik | A61B 17/0057 606/215 |
| 2012/0022573 A1* | 1/2012 | Kratzberg | A61B 17/12022 606/194 |
| 2012/0197284 A1 | 8/2012 | Ogle et al. | |
| 2013/0116720 A1* | 5/2013 | Theobald | A61B 17/0057 606/191 |
| 2013/0253632 A1 | 9/2013 | Schreck | |
| 2014/0214073 A1 | 7/2014 | Bodewadt et al. | |
| 2014/0330303 A1 | 11/2014 | Hansen | |

OTHER PUBLICATIONS

Idrees, Jahanzaib, et al. "Outcomes after false lumen embolization with covered stent devices in chronic dissection." *Journal of vascular surgery* 60.6 (2014): 1507-1513.

Kolbel, Tilo, et al. "Addressing Persistent False Lumen Flow in Chronic Aortic Dissection: The Knickerbocker Technique." *J Endovasc Ther* 21 (2014): 117-122.

San Norberto, Enrique María, et al. "Coil embolization of persistent false lumen after stent graft repair of type B aortic dissection." *Journal of vascular surgery* 54.1 (2011): 201-204.

Roselli, Eric E., et al. "Use of covered stent devices for false lumen embolization in chronic dissection: a novel approach." *The Annals of thoracic surgery* 98.2 (2014): 737-739.

* cited by examiner

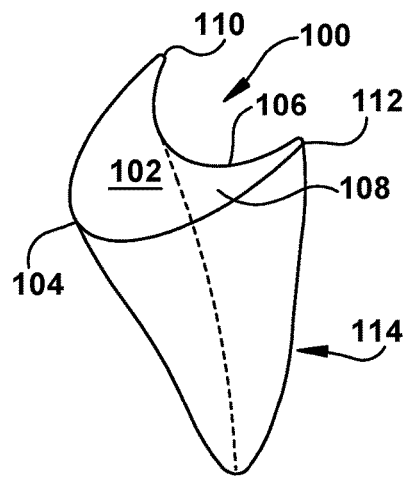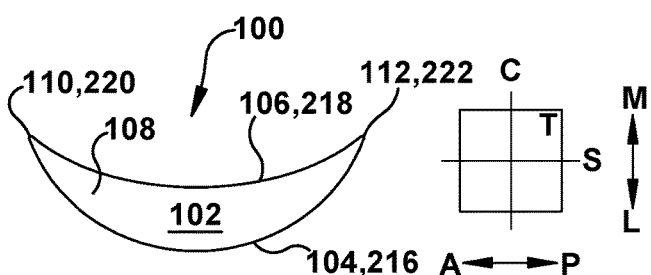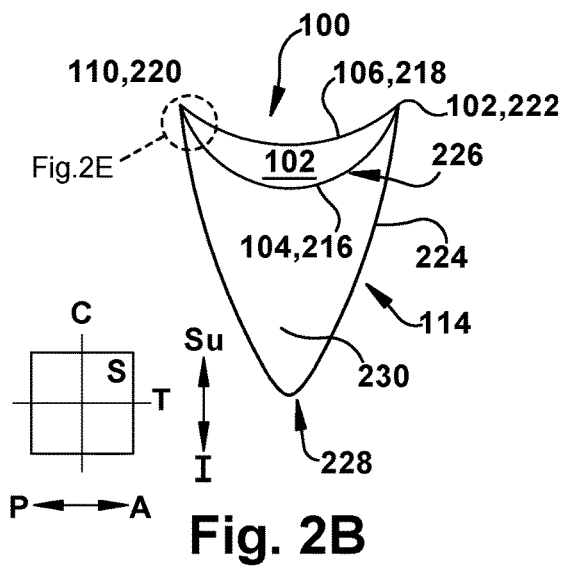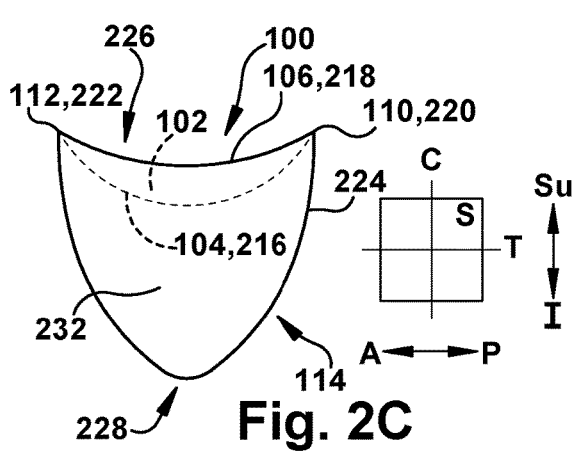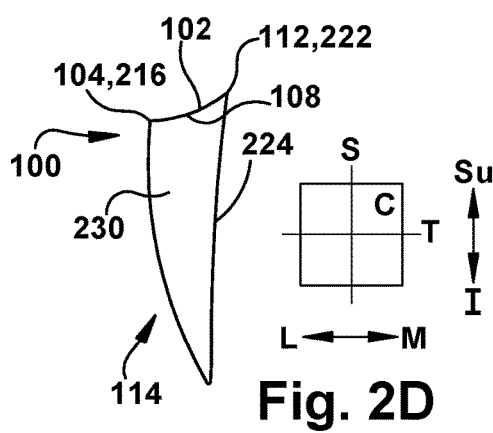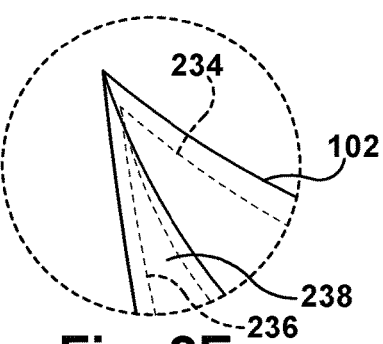

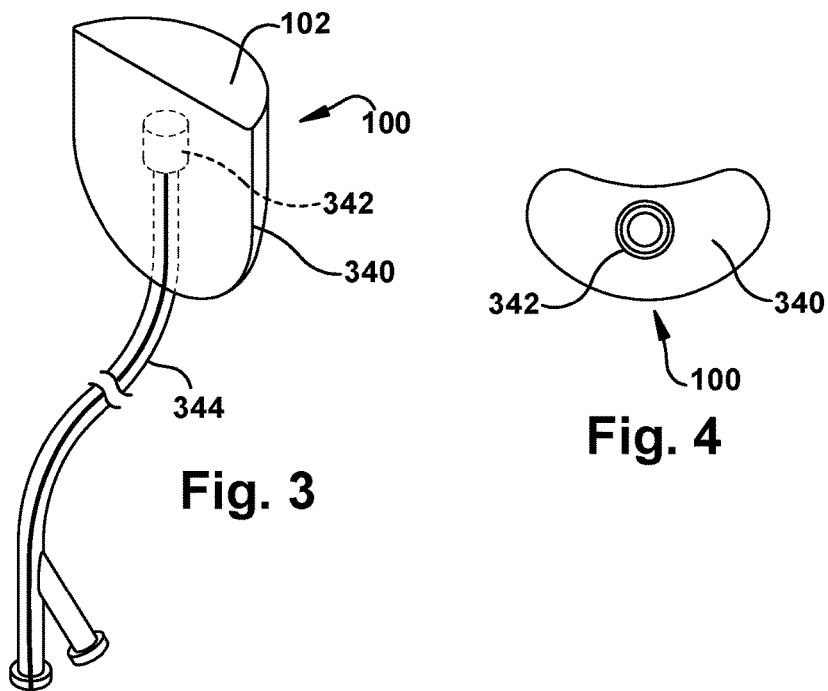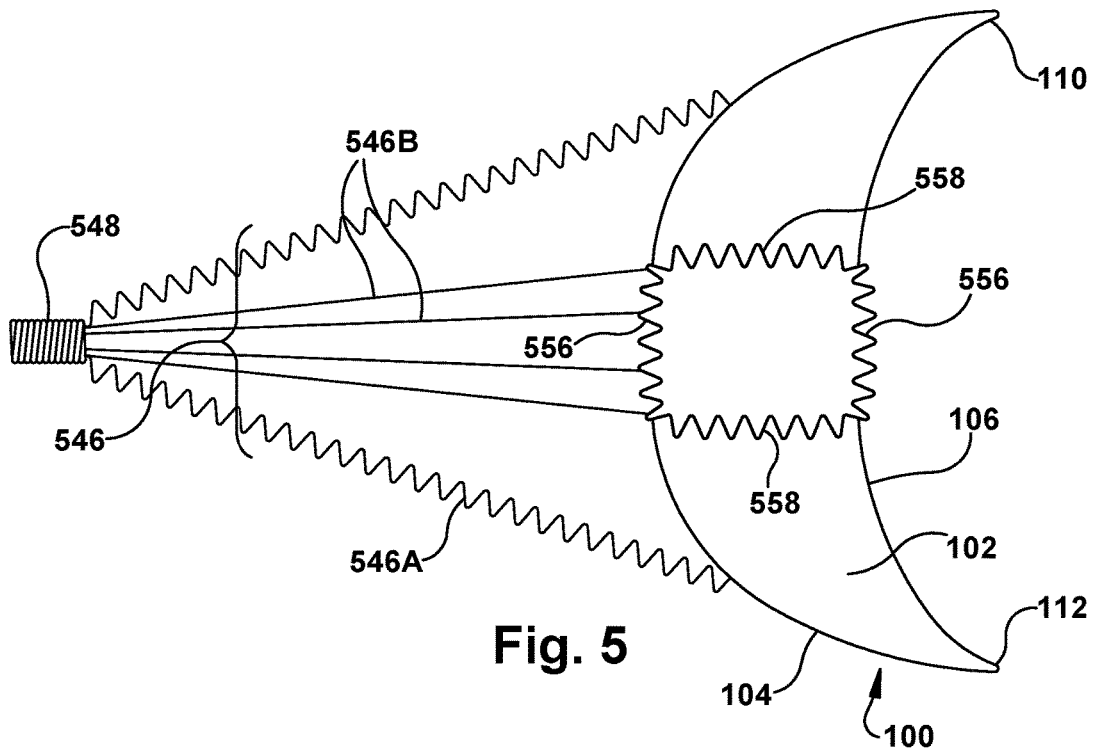

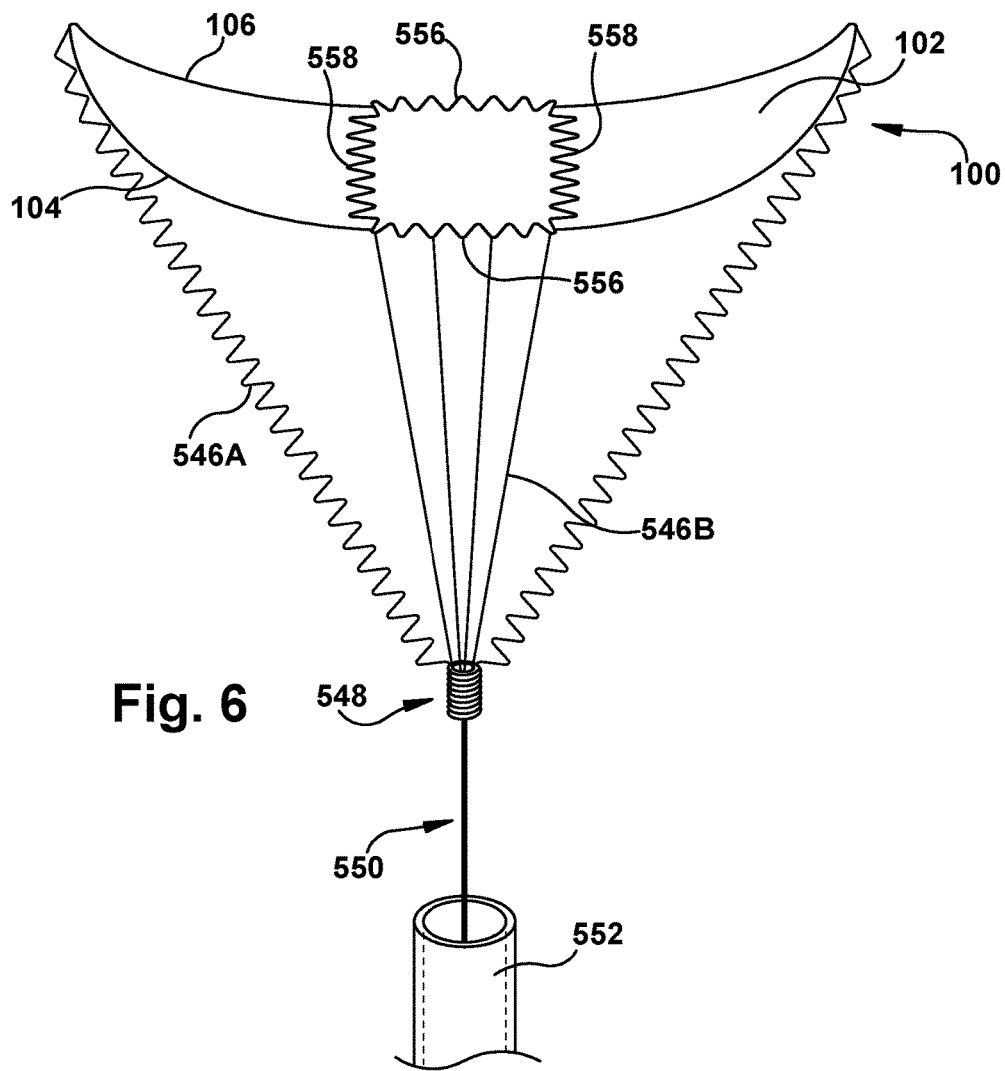
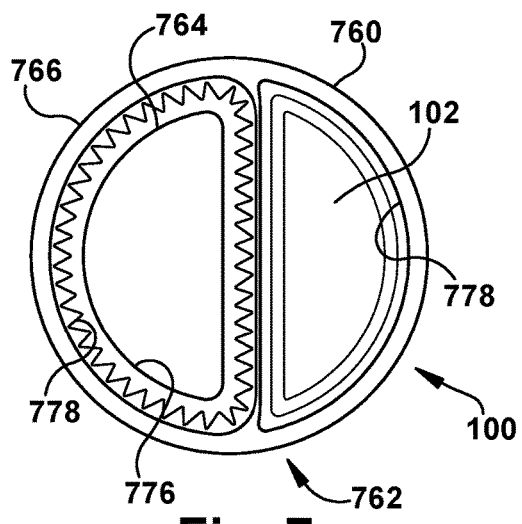
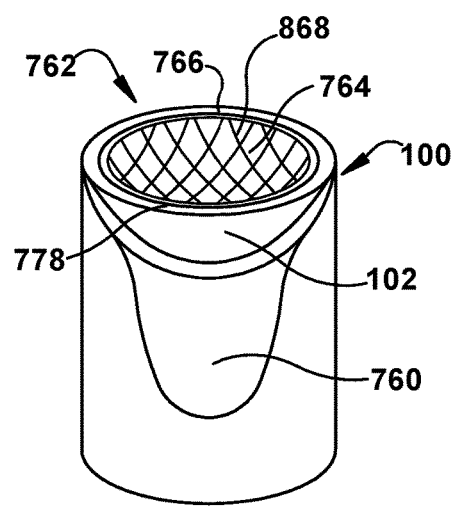

METHOD AND APPARATUS FOR SUBSTANTIALLY BLOCKING BLOODFLOW THROUGH A DISSECTED AORTA

RELATED APPLICATION

This application claims priority from U.S. Provisional Application No. 62/337,373, filed 17 May 2016, the subject matter of which is incorporated herein by reference in its entirety.

TECHNICAL FIELD

This disclosure relates to an apparatus and method for substantially blocking bloodflow through a dissected aorta and, more particularly, to a method and apparatus of providing an implantable expandable device for substantially blocking bloodflow through a false lumen of a dissected aorta.

BACKGROUND

The aorta is the major artery that carries blood from the heart to the rest of the body.

Aortic dissection occurs when the inner layer of the aortic wall (intima) tears, leading to blood flow through the tear, causing separation of the middle and inner layers of the artery wall (dissection). When blood flow dissects the artery wall, it forms a second channel for flow, creating what is termed a "false lumen". The original flow lumen in the aorta is termed the "true lumen". These two channels compete for blood flow, sometimes leading to poor or absent flow in the true lumen, which can impede perfusion of vital structures downstream such as the renal and visceral arteries. When perfusion of important arteries is impaired, this is termed "complicated" dissection. This can occur in any artery, but most often develops in areas of high pressure and shear stress like the ascending aorta (the first segment of the aorta), where the aorta originates from the heart's left ventricle (pumping chamber). This is the part of the aorta closest to the heart, hence the name "proximal aorta". Aortic dissection can also occur in other parts of the aorta.

The main risk factors for development of aortic dissection are atherosclerosis (hardening of the arteries) and high blood pressure. According to the American Heart Association, high blood pressure is the most common factor predisposing the aorta to dissection. Preventive measures to reduce and control blood pressure and reduce atherosclerosis can reduce the risk of developing aortic dissection. In addition, traumatic injury is a major cause of aortic dissection, especially blunt trauma to the chest or deceleration injury leading to aortic lining tears. Other risk factors and conditions associated with the development of aortic dissection include bicuspid aortic valve, coarctation (narrowing) of the aorta, connective tissue disorders, Ehlers-Danlos syndrome, heart surgery or procedures, Marfan syndrome, pregnancy, pseudoxanthoma elasticum, aortic dilation, aortic aneurysm, and congenital aortic valve abnormalities.

Acute aortic dissection can cause sudden chest, back, or abdominal pain. This pain is often described as a tearing sensation, and can be severe. The pain may be localized to the front or back of the chest. Other symptoms and signs depend on the arterial branches involved and compression of nearby organs. Men are more prone to develop aortic dissection (male-to-female ratio ranges from 2:1 to 5:1). Aortic dissection occurs in roughly 2 out of every 10,000 people, although some estimates are significantly higher.

Acute aortic dissection is an emergency condition, and medical treatment should start as soon as possible. The patient often is admitted to an intensive care unit, and drugs to lower blood pressure and heart rate are given. In some cases emergency surgery is needed. Alternative procedures, such as placing a stent inside the aorta, are being used more frequently. The goal of treatment is to prevent complications. Hospitalization generally is required. Surgery to repair or replace the damaged section of aorta can treat the condition in some cases. If the aortic valve is damaged, valve replacement may be necessary. If the heart arteries are involved, a coronary bypass may also be performed. Aortic dissection is a life threatening disease. The condition can be cured with surgery if it is done before the aorta ruptures or organs fail from low blood flow. Most patients who have rupture after aortic dissection do not survive. Complications from aortic dissection can include aortic aneurysm formation with or without rupture, aortic valve compromise, stroke, paralysis, kidney failure, limb loss, bowel compromise and death.

SUMMARY

In an aspect, an implantable expandable device for substantially blocking bloodflow through a false lumen of a dissected aorta is provided. An occluding surface is oriented substantially in a transverse plane. The occluding surface is bounded by a lateral occluding surface edge and a medial occluding surface edge. The lateral occluding surface edge has a first radius of curvature which is positively curved toward the lateral direction. The medial occluding surface edge has a second radius of curvature which is positively curved toward the lateral direction. The second radius of curvature is larger than the first radius of curvature. The occluding surface has an occluding surface body located transversely between the lateral and medial occluding surface edges. A supporting structure is located entirely inferiorly to the occluding surface. The supporting surface includes a plurality of struts extending substantially in the superior-inferior direction. At least a first one of the struts is a full-height strut and spans substantially a full superior-inferior height of the device. At least a second one of the struts is a reduced-height strut and spans substantially less than a full superior-inferior height of the device. The occluding surface substantially occludes a transverse cross-section of the false lumen to substantially block bloodflow in the superior-inferior direction within the false lumen.

In an aspect, a method of substantially blocking bloodflow through a false lumen of a dissected aorta is provided. An implantable expandable device is provided for substantially blocking bloodflow through the false lumen. The device is configured for selective movement between collapsed and expanded device conditions. The device includes an occluding surface oriented substantially in a transverse plane. The occluding surface is bounded by a lateral occluding surface edge and a medial occluding surface edge. The lateral occluding surface edge has a first radius of curvature which is positively curved toward the lateral direction. The medial occluding surface edge has a second radius of curvature which is positively curved toward the lateral direction. The second radius of curvature is larger than the first radius of curvature. The occluding surface has an occluding surface body located transversely between the lateral and medial occluding surface edges. A supporting structure is located entirely inferiorly to the occluding surface. The supporting surface includes a plurality of struts extending substantially in the superior-inferior direction. At least a first one of the struts is a full-height strut and spans substantially a full superior-inferior height of the device. At least a second one of the struts is a reduced-height strut and spans substantially less than a full superior-inferior height of the device. The occluding surface substantially occludes a transverse cross-section of the false lumen to substantially block bloodflow in the superior-inferior direction within the false lumen. The device is passed, in the collapsed condition, through a vasculature of the patient. The device, in the collapsed condition, is placed substantially in the desired deployment position within the false lumen. The device is expanded within the false lumen. The device is maintained in the desired deployment position in the expanded condition. When the device is in the expanded condition within the false lumen, a transverse cross-section of the false lumen is substantially occluded with the occluding surface to substantially block bloodflow in the superior-inferior direction within the false lumen.

BRIEF DESCRIPTION OF THE DRAWINGS

For a better understanding, reference may be made to the accompanying drawings, in which:

FIG. 1 is a schematic perspective view of an aspect of the present invention;

FIG. 2A is a top view of the aspect of FIG. 1;

FIG. 2B is a front view of the aspect of FIG. 1;

FIG. 2C is a rear view of the aspect of FIG. 1;

FIG. 2D is a side view of the aspect of FIG. 1;

FIG. 2E is a phantom-line partial detail taken of area "E" in FIG. 2B;

FIG. 3 is a perspective view of the aspect of FIG. 1 in an example configuration;

FIG. 4 is a bottom view of the aspect of FIG. 1 in the example configuration of FIG. 3;

FIG. 5 is a top view of the aspect of FIG. 1 in another example configuration;

FIG. 6 is a perspective side view of the aspect of FIG. 5 in an example use environment;

FIG. 7 is a top view of any aspect of the present invention in an example use environment;

FIG. 8 is a perspective side view of any aspect of the present invention in the example use environment of FIG. 7;

DESCRIPTION OF ASPECTS OF THE DISCLOSURE

Figure 9A:
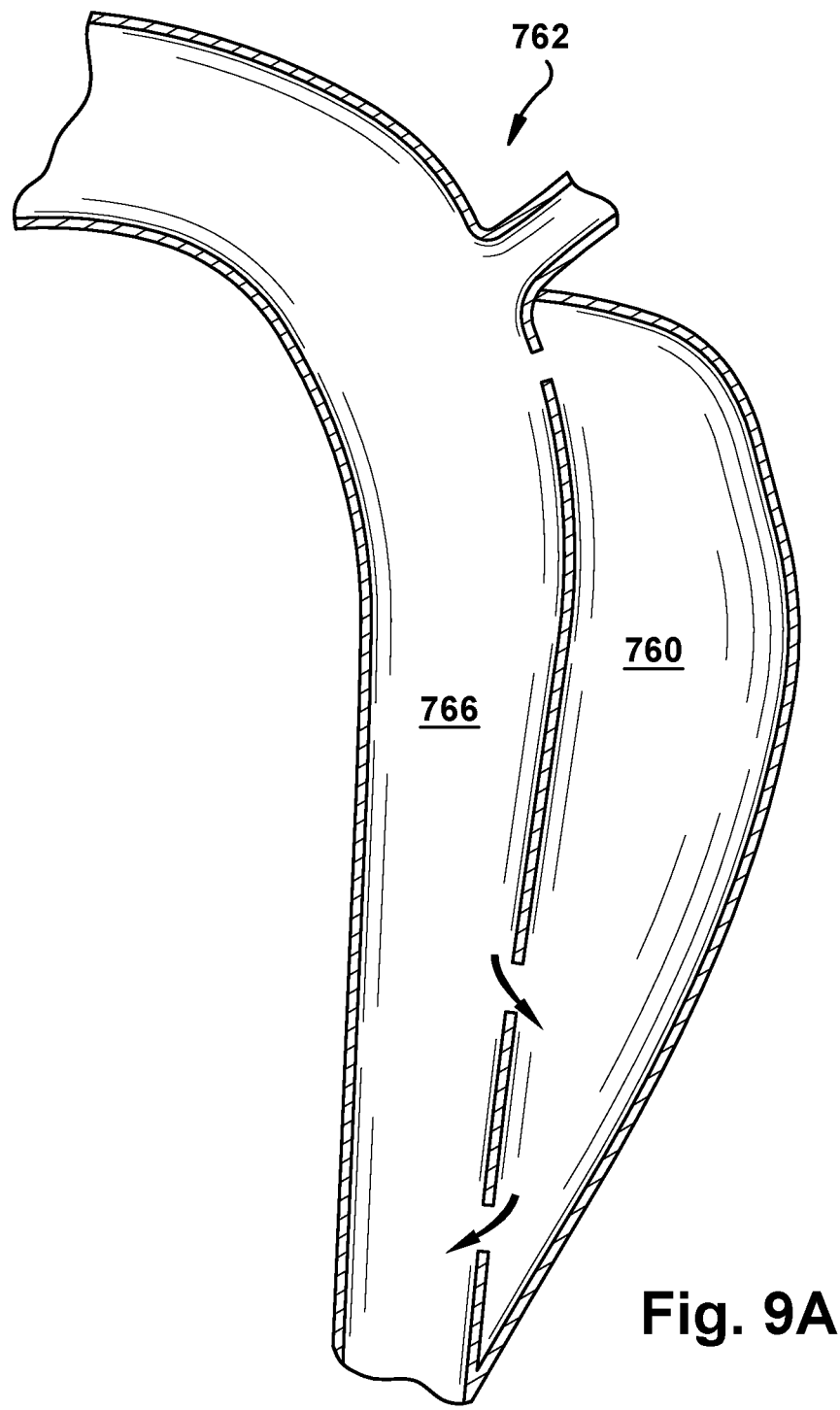
FIGS. 9A-9E schematically depict the placement of the aspect of any Figure or embodiment described and shown herein into the example use environment of FIG. 5.

Unless defined otherwise, all technical and scientific terms used herein have the same meaning as is commonly understood by one of skill in the art to which the present disclosure pertains.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, farm animals, livestock, etc.

As used herein, the terms "treat" or "treating" can refer to therapeutically regulating, preventing, improving, alleviating the symptoms of and/or reducing the effects of a dissected aorta. As such, treatment also includes situations where a dissected aorta, or at least a symptom associated therewith, is completely inhibited, e.g., prevented from happening or stopped (e.g., terminated) such that the subject no longer suffers from the dissected aorta, or at least the symptom(s) associated therewith.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature may not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

The invention comprises, consists of, or consists essentially of the following features, in any combination.

FIG. 1 depicts an implantable expandable device 100 for substantially blocking bloodflow through a false lumen of a dissected aorta. The device 100 is configured for selective movement between collapsed and expanded device conditions, as will be discussed below. An occluding surface 102 is oriented substantially in a transverse plane. The transverse plane (T) is substantially along the plane of the page in FIG. 2A. The transverse plane (T), coronal plane (C), sagittal plane (S), lateral direction (L), medial direction (M), anterior direction (A), posterior direction (P), inferior direction (I), and superior direction (Su) are used herein for clarity of orientation, and are clearly indicated in FIGS. 2A-2E. In use, the occluding surface 102 substantially occludes a transverse cross-section of the false lumen to substantially block bloodflow in the superior-inferior direction within the false lumen.

The occluding surface 102 is bounded by a lateral occluding surface edge 104 and a medial occluding surface edge 106. The lateral occluding surface edge 104 has a first radius of curvature which is positively curved toward the lateral direction. The medial occluding surface edge 106 has a second radius of curvature which is positively curved toward the lateral direction. The second radius of curvature is larger than the first radius of curvature, to provide the occluding surface 102 with a crescent moon shape, when viewed from the superior direction, as shown in FIG. 2A.

The occluding surface 102 has an occluding surface body 108 located transversely between the lateral and medial occluding surface edges 104 and 106. The occluding surface 102 includes an anterior surface apex 110 formed at an anterior junction of the lateral and medial occluding surface edges 104 and 106 and a posterior surface apex 112 formed at a posterior junction of the lateral and medial occluding surface edges 104 and 106.

For any configuration or option of the occluding surface, the anterior and posterior surface apices 110 and 112 may both be positioned substantially superiorly to a majority of the occluding surface 102, as shown particularly in FIGS. 1 and 2B. Similarly for any configuration or option of the occluding surface 102, and as clearly shown in the same Figures, a majority of the lateral occluding surface edge 104 may be located inferiorly to a majority of the medial occluding surface edge 106.

At least a portion of the occluding surface may include a surface treatment configured to promote thrombosis including, but not limited to, homocysteine, prothrombin, any therapeutic agent provided to and/or impregnated into the occluding surface material, a surface texture, any other surface treatment, and/or any combination thereof.

The device 100 also has a supporting structure 114 located entirely inferiorly to the occluding surface 102. That is, all portions of the supporting structure 114 are located inferiorly to transversely corresponding portions of the occluding surface 102—one of ordinary skill in the art will understand that, depending upon the curvature of the occluding surface 102 in the superior-inferior direction, there may be portions of the supporting structure 114 that are located at a similar height to, or even superiorly to, transversely spaced portions of the occluding surface 102. Optionally, the occluding surface 102 and supporting structure 114 may mutually comprise the shape of a barchan (sand) dune, similar to that shown at https://upload.wikimedia.org/wikipedia/commons/thumb/3/33/Barchan.jpg/400px-Barchan.jpg (last visited 27 Apr. 2017).

As shown in at least FIGS. 1-4, and as described in this paragraph with specific reference to FIGS. 2A-2E, the supporting structure 114 may include an upper lateral supporting structure surface edge 216, which is substantially coincident with the lateral occluding surface edge 104, and an upper medial supporting structure surface edge 218. The upper medial supporting structure surface edge 218 is substantially coincident with the medial occluding surface edge 106 and contacts the upper lateral supporting structure surface edge 216 both at an anterior supporting structure apex 220 (formed at an anterior junction of the upper lateral and medial supporting structure edges 216 and 218) and at a posterior supporting structure apex 222 (formed at a posterior junction of the upper lateral and medial supporting structure edges 216 and 218). The supporting structure 114 may also include a substantially parabolic supporting structure side edge 224, having an upper side edge gap 226 opening in the superior direction and sagittally spaced from a closed lower side edge apex 228. The supporting structure side edge 224 connects, and extends inferiorly from, the anterior and posterior supporting structure apices 220 and 222. The supporting structure 114 also may include a sagittally oriented lateral supporting structure surface 230, extending between the supporting structure side edge 224 and the upper lateral supporting structure surface edge 216. A sagittally oriented medial supporting structure surface 232 of the supporting structure 114 extends between the supporting structure side edge 224 and the upper medial supporting structure surface edge 218.

Optionally, the lateral supporting structure surface 230 may extend between the supporting structure side edge 224 and the upper lateral supporting structure surface edge 216 with no intervening structures. The medial supporting structure surface 232, likewise, may extend between the supporting structure side edge 224 and the upper medial supporting structure surface edge 218 with no intervening structures. The lateral supporting structure surface 230 may have a third radius of curvature, taken at a predetermined superior-inferior position, which is positively curved toward the lateral direction. The medial supporting structure surface 232 may have a fourth radius of curvature, taken at the same superior-inferior position as that at which the third radius of curvature is taken, which is positively curved toward the lateral direction. The fourth radius of curvature may be larger than the third radius of curvature to provide the supporting structure 114, as a whole, with a crescent moon-shaped cross-section taken in a transversely-oriented plane.

A device 100 having the structure described above may be provided in a number of different ways. As a first ("stent-graft") option, and as shown in the phantom-line detail view of FIG. 2E, the device 100 may include a semi-rigid surface support member 234 underlying a flexible occluding surface 102. The supporting structure 114 may include a semi-rigid supporting structure frame 236 underlying a flexible supporting structure outer surface 238, to facilitate transition between the collapsed and expanded conditions of the device 100. For example, the semi-rigid structures may be self-expanding and/or force (e.g., balloon) expanded stent structures made of any suitable material including, but not limited to, plastics, metals, and shape-memory materials such as NiTinol. The flexible occluding surface 102 and/or supporting structure outer surface 238 may also be made of any suitable material including, but not limited to, cloth, plastic, polytetrafluoroethylene, polyethylene terephthalate, polyester woven fabrics, and synthetic and/or natural tissues. The flexible occluding surface 102 and supporting structure outer surface 238 should be made from a biocompatible material for most use environments of the device 100.

As another option, and as specifically shown in FIGS. 3-4, the occluding surface and the supporting structure may be collectively formed by a single inflatable balloon 340 configured to selectively maintain the barchan dune shape of the device 100. This barchan dune shape may be maintained in the absence of external shaping structure, such as via the device 100 including an at least semi-rigid framework (not shown) associated with the balloon 340 (internally and/or externally), via a "presetting" (e.g., heat setting or fabrication from shaped panels) of the balloon 340 during preparation for use, or in any other desired manner. Stated differently, while the balloon 340 may be somewhat flexible or resilient to custom-fit the general "barchan dune" shape shown in at least FIGS. 1-4 to at least a portion of a particular patient's false lumen shape/volume, the balloon 340 is not reliant upon pressure from the false lumen walls to achieve the barchan dune shape itself, but—when the device 100 is in the expanded position—will hold a shape similar to that shown in at least FIG. 1 in the absence of any surrounding pressure/structures.

The balloon 340 may include a selectively operable inflation valve 342 configured to accept inflation fluid, to facilitate inflation of the balloon 340 from the collapsed to the expanded condition once the device 100 is arranged at a predetermined location in the false lumen. The inflation valve 342 may be selectively attachable to an inflation catheter 344, such as via a valved screw connection or any other suitable attachment means permitting passage of inflation fluid therethrough. As shown in FIG. 3, the inflation catheter 344 may be used to facilitate placement and manipulation of the device 100 inside the patient's body.

Another option for a device 100 configuration is shown in FIGS. 5-6. In this version, the supporting structure 114 includes a plurality of anchor strands 546. Each anchor strand 546 extends between a selected one of the lateral occluding surface edge 104 and the medial occluding surface edge 106, and an anchor hub 548 located inferior to the occluding surface. Optionally, variable-length anchor strands 546A extend between each of the anterior and posterior surface apices 110 and 112 and any anchor hub 548 which is present, and at least one fixed-length anchor strand 546B extends between a selected one of the lateral occluding surface edge 104 and the medial occluding surface edge 106, and the anchor hub 548.

The occluding surface 102 shown in FIGS. 5-6 could be made substantially from a solid "sheet" of material (of any desired flexibility), could be a self- or force-expandable stent covered with a flexible cloth, or could have any other desired configuration.

The anchor strands 546, when present, may form a detachable support structure 114, used during placement of the occluding surface 102 in the desired position within the false lumen. For example, the occluding surface 102 could be deployed from a delivery catheter 550, with the anchor hub 548 being connected to the delivery catheter 550. The anchor strands 546 would accordingly be configured to be released from the occluding surface 102 and to be retracted into the delivery catheter 550, or into an outer sheath 552 associated therewith for removal from the patient's body once the occluding surface 102 is in place as desired.

It is also contemplated that, when the support structure 114 includes anchor strands 546 and an anchor hub 548, the anchor hub 548 could be released from the delivery catheter 550, allowing the support structure 114 to remain as an indwelling portion of the device 100. For example, portions or all of the support structure 114 could be permitted ingrowth into the patient tissue in or near the false lumen to assist with anchoring the device 100 as desired. While the anchor hub 548 remains attached to the delivery catheter 550, the combination of the anchor strands 546 and anchor hub 548 can be used to facilitate any desired recapture and repositioning. The anchor hub 548 can be releasably attached to the delivery catheter 550 in any suitable manner, including, but not limited to, hub-and-screw, trigger wire, and hook-and-pin concepts.

To place and maintain the occluding surface 102 shown in FIGS. 5-6 into a desired position for occluding the false lumen, the occluding surface 102 is released from the collapsed condition in a delivery catheter 550 and/or an outer sheath 552, through which it was transported into the patient's body. The variable-length anchor members 546A, when present, may be spring-shaped or otherwise configured to exert a biasing force tending to push the anterior and posterior surface apices 110 and 112 into a desired position within the false lumen and into the expanded condition. The expansion of the anterior and posterior surface apices 110 and 112 could also or instead occur due to the radial forces developed within a shape-memory device. The occluding surface 102 should be, for most use environments, slightly oversized relative to a cross-section of the false lumen at the installation location, such that the occluding surface 102 pushes against the false lumen walls (likely with a transversely-oriented force) into an interference fit that holds the occluding surface 102 in place, even after any removal of the anchor strands 546. When the occluding surface 102 is configured to promote thrombosis and/or ingrowth with the false lumen walls, such will reinforce the "anchoring" provided by the interference fit.

Optionally, and as shown in FIGS. 5-6, at least a chosen one of the lateral occluding surface edge 104 and the medial occluding surface edge 106 may include an A-P expansion feature 556 (e.g., a spring and/or a shape memory or self-expanding structure) biased to extend the chosen occluding surface edge 104 and/or 106 in the anterior-posterior direction. Also optionally, the occluding surface 102 may include at least one substantially coronally oriented L-M expansion feature 558 biased to extend the occluding surface 102 in the lateral-medial direction. When A-P and/or L-M expansion features 556 and 558 are present, at least a portion of the occluding surface 102 between these features may be pleated, elastic, or otherwise configured to stretch to accommodate any expansion of the surface caused by these features.

FIGS. 7-8 depict a device 100, according to any configuration or option described herein, in place within a false lumen 760. As can be seen in these Figures, the occluding surface 102 substantially blocks bloodflow through the false lumen 760 of a dissected aorta 762, and an implantable true lumen stent-graft 764 substantially maintains bloodflow through the true lumen 766 of the dissected aorta 762. That is, and as shown further in FIG. 8 and in FIGS. 9D-9E, the true lumen stent-graft 764 includes a semi-rigid, expandable stent-graft frame 868 having a tubular frame body 970 extending sagittally between open superior and inferior frame ends 972 and 974, respectively. A tubular flexible stent-graft liner 776 is maintained within and/or around the tubular frame body 970, such that the stent-graft liner 776 is mainly (if not wholly) located on a chosen one of the outside and the inside of the tubular frame body 970. The true lumen stent-graft 764 exerts outward pressure upon at least a portion of a transverse cross-section of the true lumen 766, when the true lumen stent-graft 764 is present therein, to substantially maintain bloodflow therethrough in the superior-inferior direction through the true lumen 766. As shown in FIGS. 7-8, then, a majority—often a supermajority—of the false lumen 760 device 100 will be oriented laterally to the entirety of the true lumen stent-graft 764 when the false lumen 760 device 100 is present in the false lumen 760 and the true lumen stent-graft 764 is present in the true lumen 766. At least one of the false lumen 760 device 100 and the true lumen stent-graft 764 may be balloon-expanded, or force-expanded, into engagement with a lumen wall 778 of a corresponding false or true lumen 760 or 766.

Figure 9B:
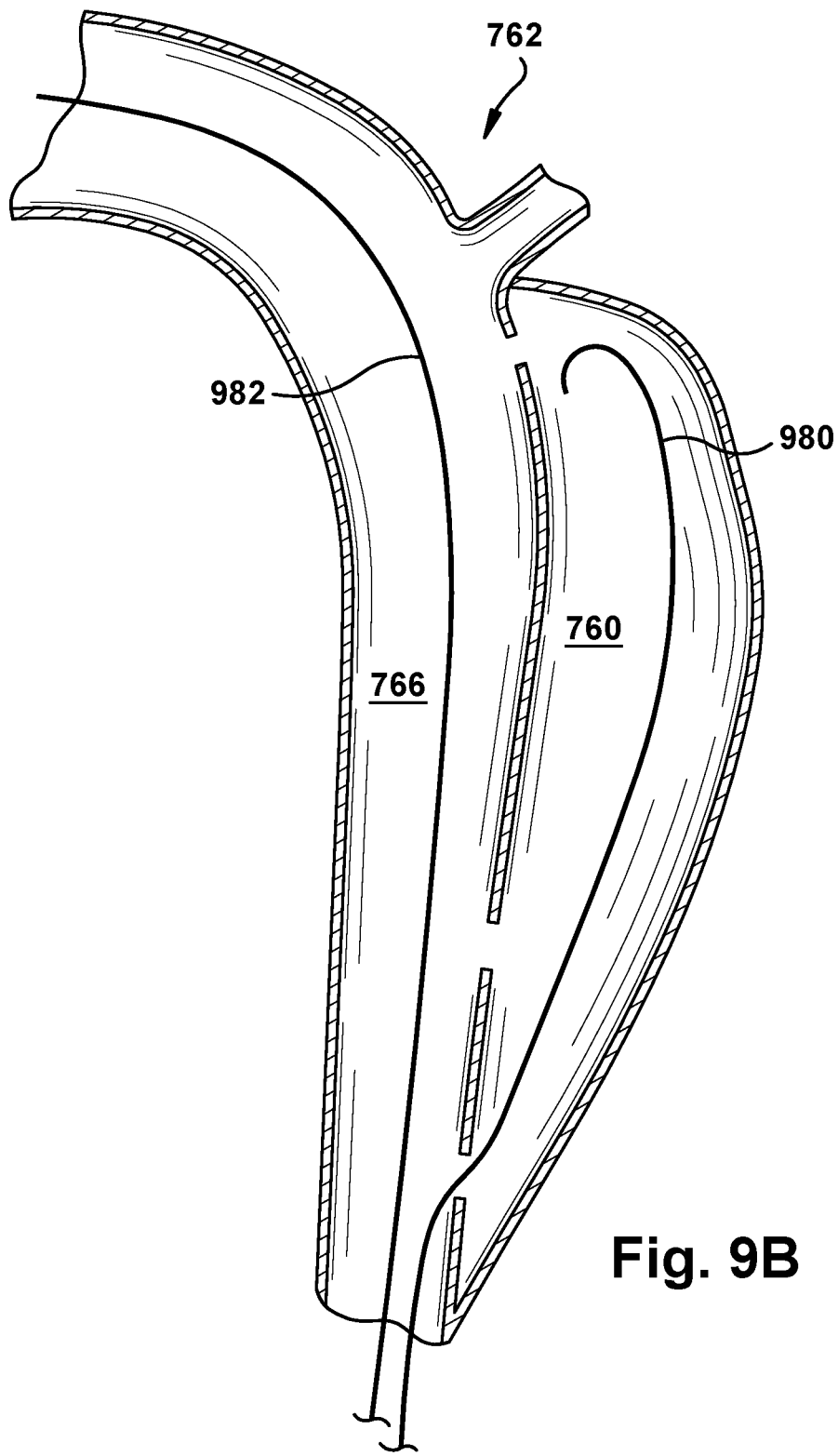

FIGS. 9A-9E depict an example sequence of installation for any configuration or aspect of the device 100, 100' described and shown herein. In FIG. 9A, the dissected aorta 762, with false and true lumens 760 and 766, is shown. In FIG. 9B (optional) false and true lumen guidewires 980 and 982, respectively, have been passed into the patient's vasculature and into the depicted positions.

Figure 9C:
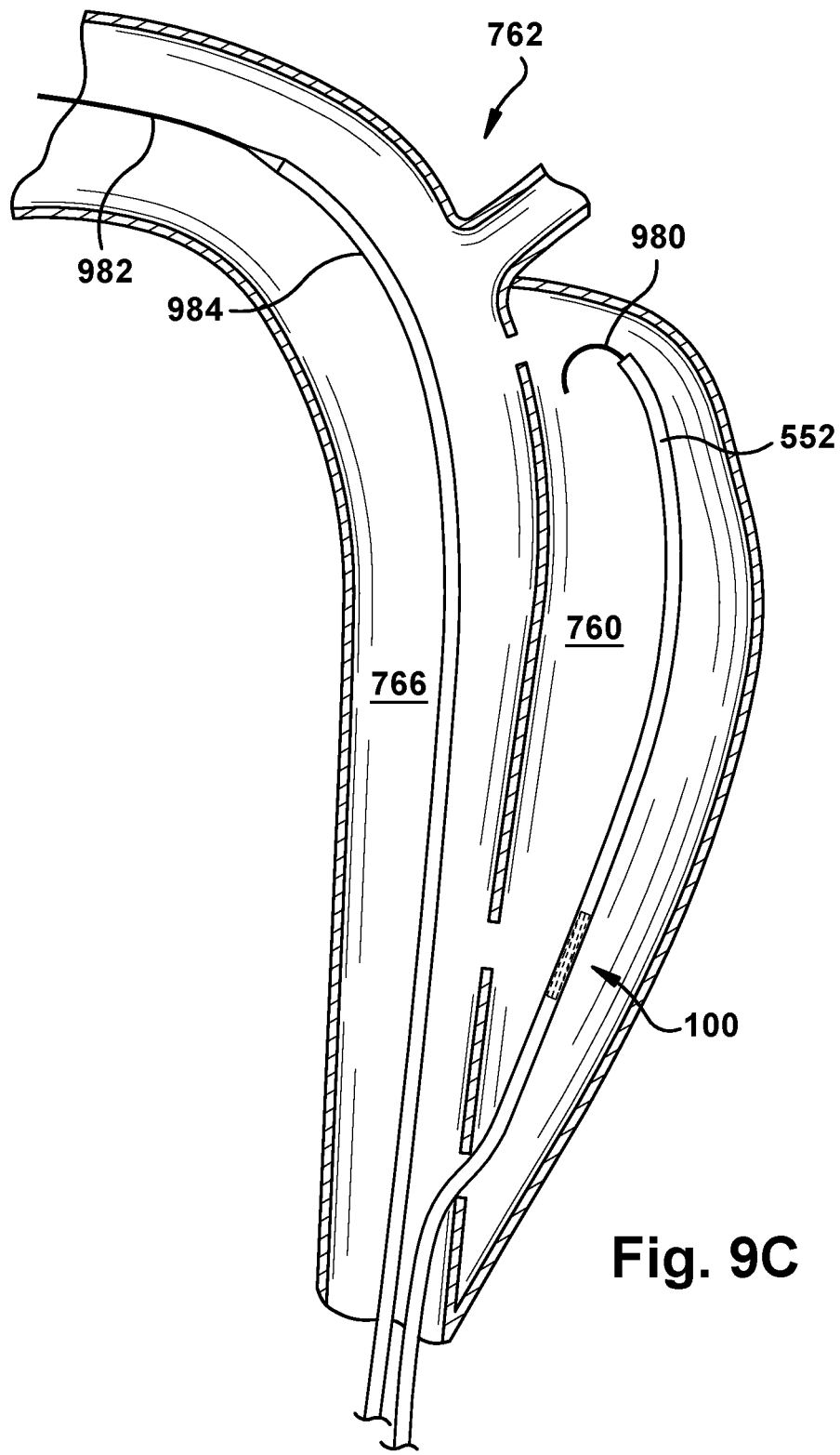

In FIG. 9C, an outer sheath 552 has been passed over the false lumen guidewire 980 and into the false lumen 760, and a true lumen sheath 984 (with the true lumen stent-graft 764 constrained therein) has been passed over the true lumen guidewire 982 and into the true lumen 766. During placement of the system into the FIG. 9C configuration, the device 100 has been passed, in the collapsed condition, through the vasculature of the patient and is held therein (shown in dotted line in FIG. 9C). The device 100, in the collapsed condition, is then placed substantially in the desired deployment position within the false lumen 760. For example, the outer sheath 552 may be manipulated in any direction within the false lumen 760 to place the collapsed device 100 as desired.

Figure 9D:
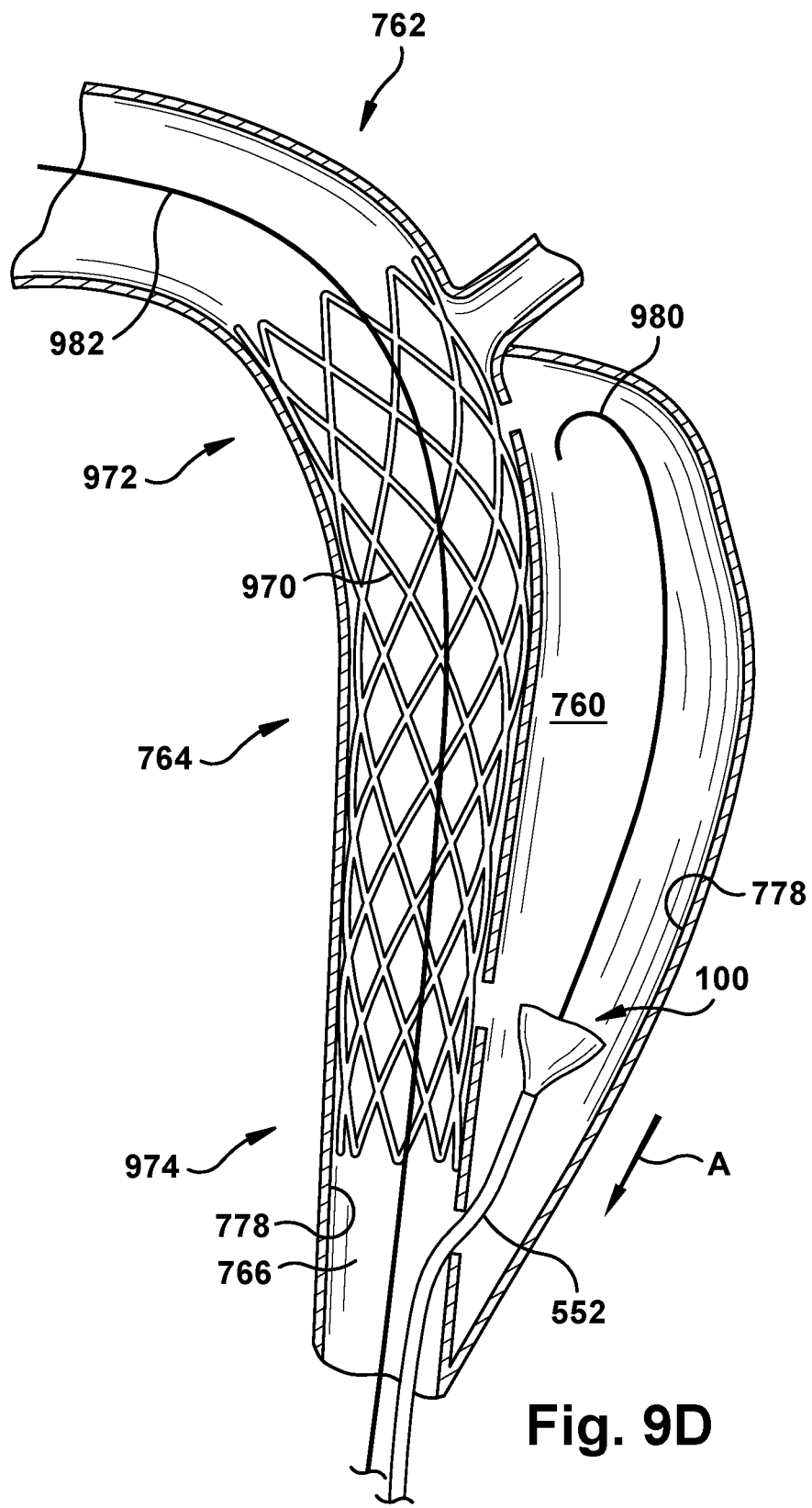

The device 100 is then expanded within the false lumen 760, as shown in FIG. 9D. For example, when at least a portion of the device 100 is self-expanding, the outer sheath 552 may be withdrawn, in the direction of arrow A, to release the device 100 therefrom. If the device 100 includes a balloon 340 (or uses a balloon-expanded structure), inflation fluid may be provided through an inflation catheter 344. One of ordinary skill in the art will be able to deploy and expand the device 100 appropriately in the desired position within the false lumen 760. The device is shown in the Figures as being located in an inferior portion of the false lumen 760, but could be located in any desired position within the false lumen 760, as suitable for a particular patient's dissected aorta 762.

Figure 9E:
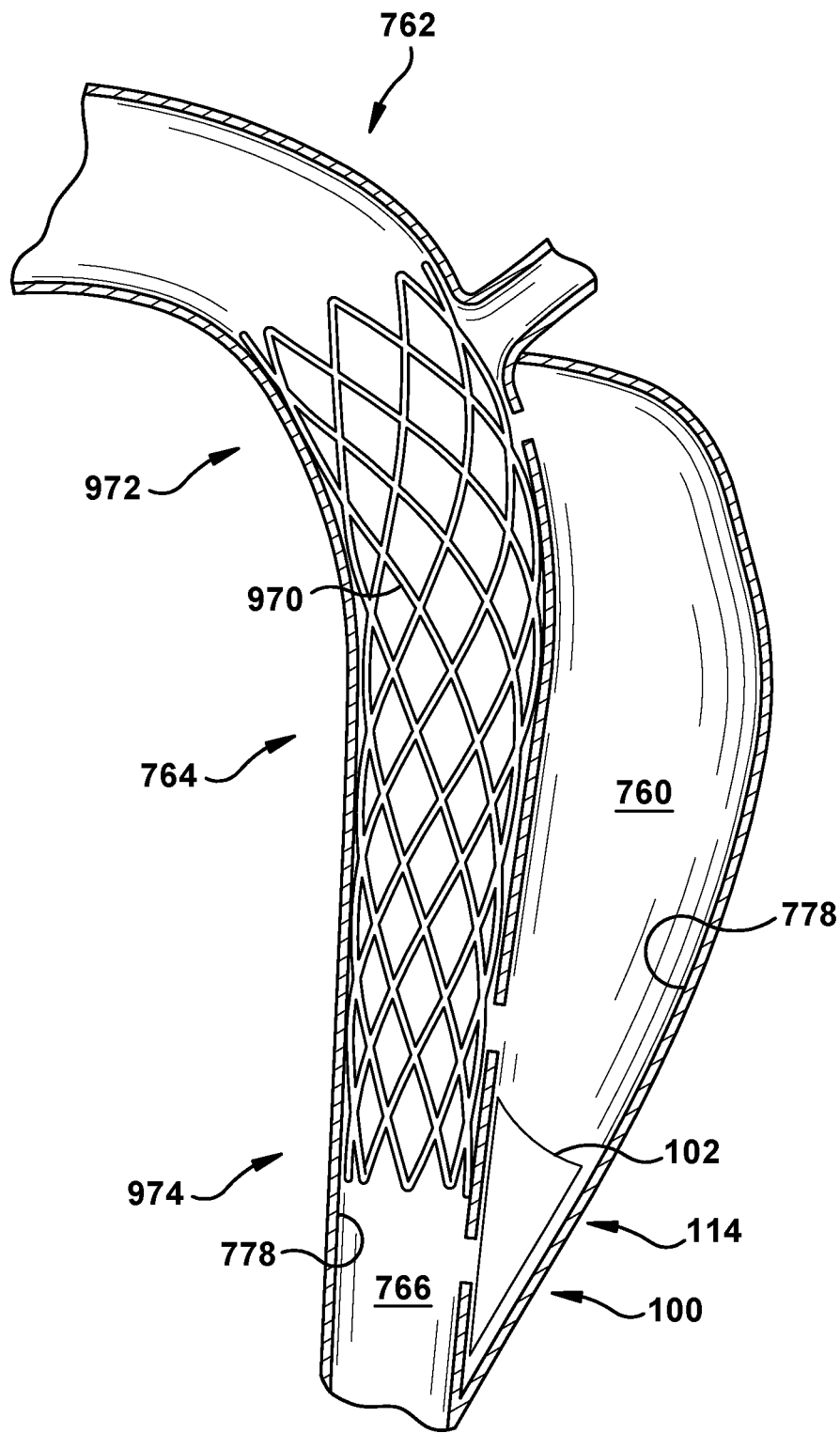

The device 100, once deployed in any suitable manner, is then maintained in the desired deployment position within the false lumen 760 in the expanded condition, as shown in FIG. 9E. This maintenance may include applying force against a lumen wall 778 of the false lumen 760 using at least one of the occluding surface 102 and a supporting structure 114.

When the device 100 is in the expanded condition within the false lumen 760, transverse cross-section of the false lumen 760 is substantially occluded with the occluding surface 102 to substantially block bloodflow in the superior-inferior direction within the false lumen 760. Over time, ingrowth and/or thrombosis will also supplement the occluding property of the occluding surface 102, as well. The device 100 is described herein as being repositionable during installation but not removable long-term (due to ingrown) for most use environments, but it is also contemplated that the device 100 could be designed to instead be removable even after a significant indwelling time (e.g., several months to several years).

When the supporting structure 114 includes anchor strands 546, the anchor strands 546 may be released from the emplaced occluding surface 102, and the anchor strands 546 may then be retracted into the delivery catheter 550 for removal from the body of the patient. For any aspect or configuration of the device 100, the outer sheath 552, true lumen sheath 984, and false and true lumen guidewires 980 and 982 will then be retracted through the patient's vasculature and removed from the patient's body.

FIGS. 10-20 illustrate a second embodiment of a device 100'. The device 100' of FIGS. 10-20 is similar to the device 100 of FIGS. 1-9E and therefore, structures of FIGS. 10-20 that are the same as or similar to those described with reference to FIGS. 1-9E have the same reference numbers with the addition of a "prime" mark. Description of common elements and operation similar to those in the previously described first embodiment will not be repeated with respect to the second embodiment.

Figure 10:
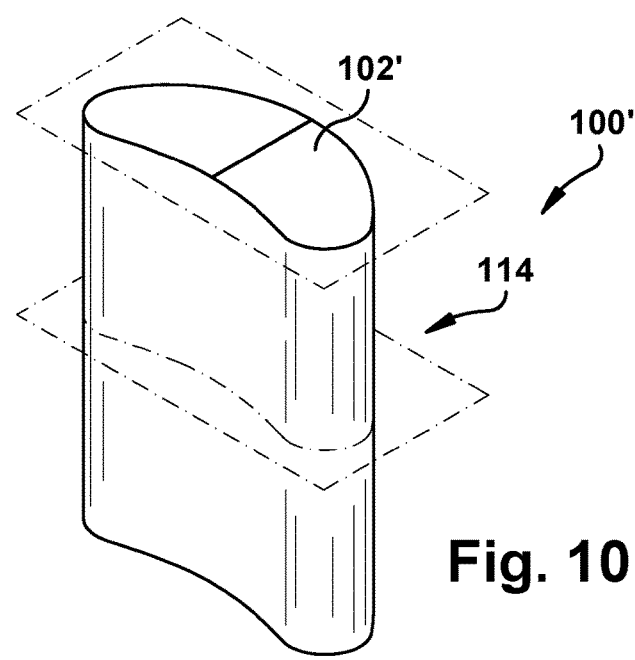
FIG. 10 is a schematic perspective top view of an aspect of the present invention.
Figure 11:
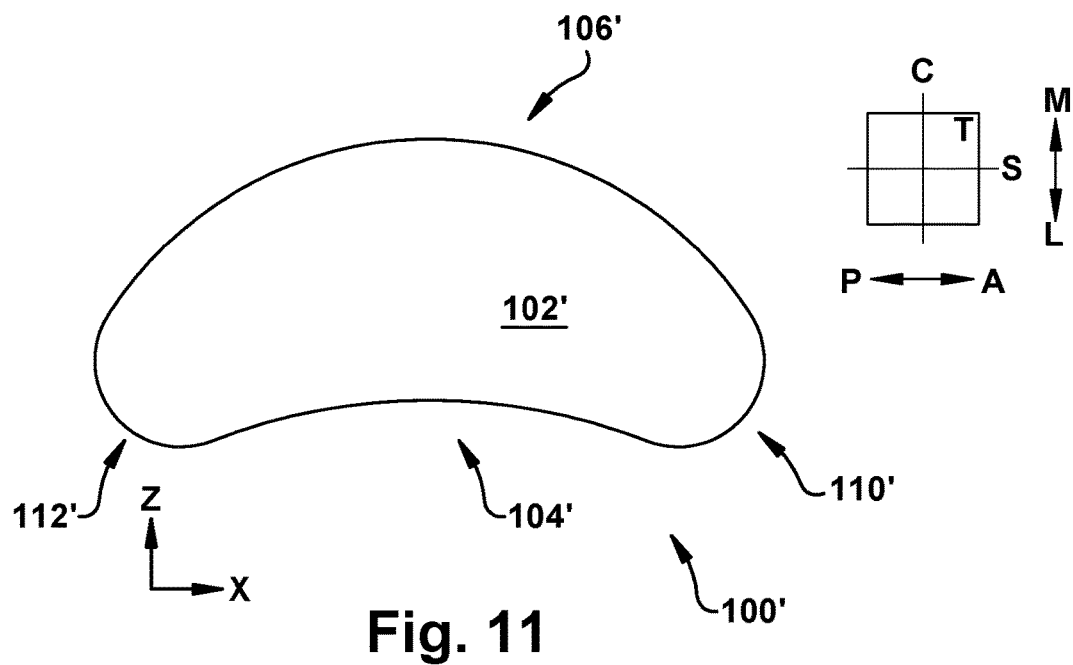
FIG. 11 is a top view of the aspect of FIG. 10.

As shown in FIGS. 10-11, the device 100' may be a cylindrical solid, albeit not a circular cylindrical solid (wherein a cylinder is a solid bounded by a closed cylindrical surface and two parallel planes). The device 100' has an occluding surface 102' with lateral and medial occluding surface edge 104' and 106'.

Figure 12:
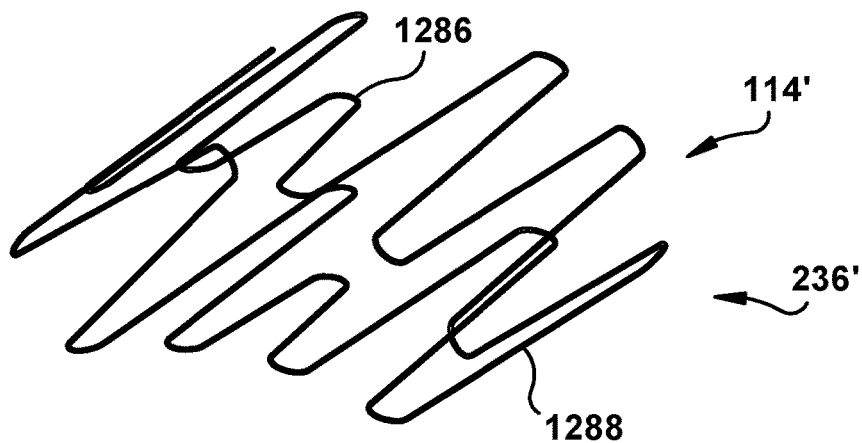
FIG. 12 is a perspective top view of a component of the aspect of FIG. 10.

The supporting structure 114' of the device 100' is partially shown in FIG. 12, which is a perspective view of the supporting structure frame 236' taken substantially in a superior-to-inferior direction. As shown in FIG. 12, the supporting structure frame 236' includes a sinuous or wave-like structure defining a plurality of reduced-height struts 1286 and full-height (of the device 100') struts 1288. This arrangement of reduced-height struts 1286 and full-height struts 1288 is provided to provide the supporting structure 114' with a desired combination of strength, flexibility, conformability, and compactability (for insertion). FIG. 12 depicts about six full-height struts 1288 and about two reduced height struts 1286.

Figure 13:
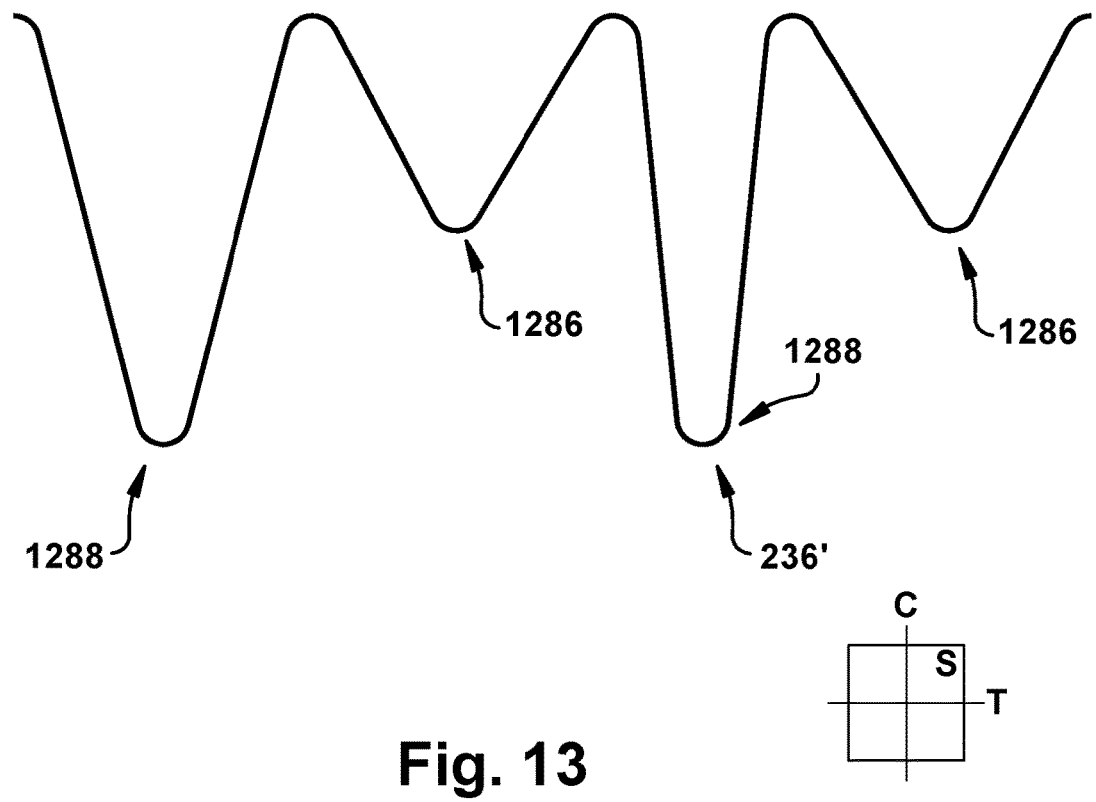
FIG. 13 is partial disassembled view of the component of FIG. 12.
Figure 14:
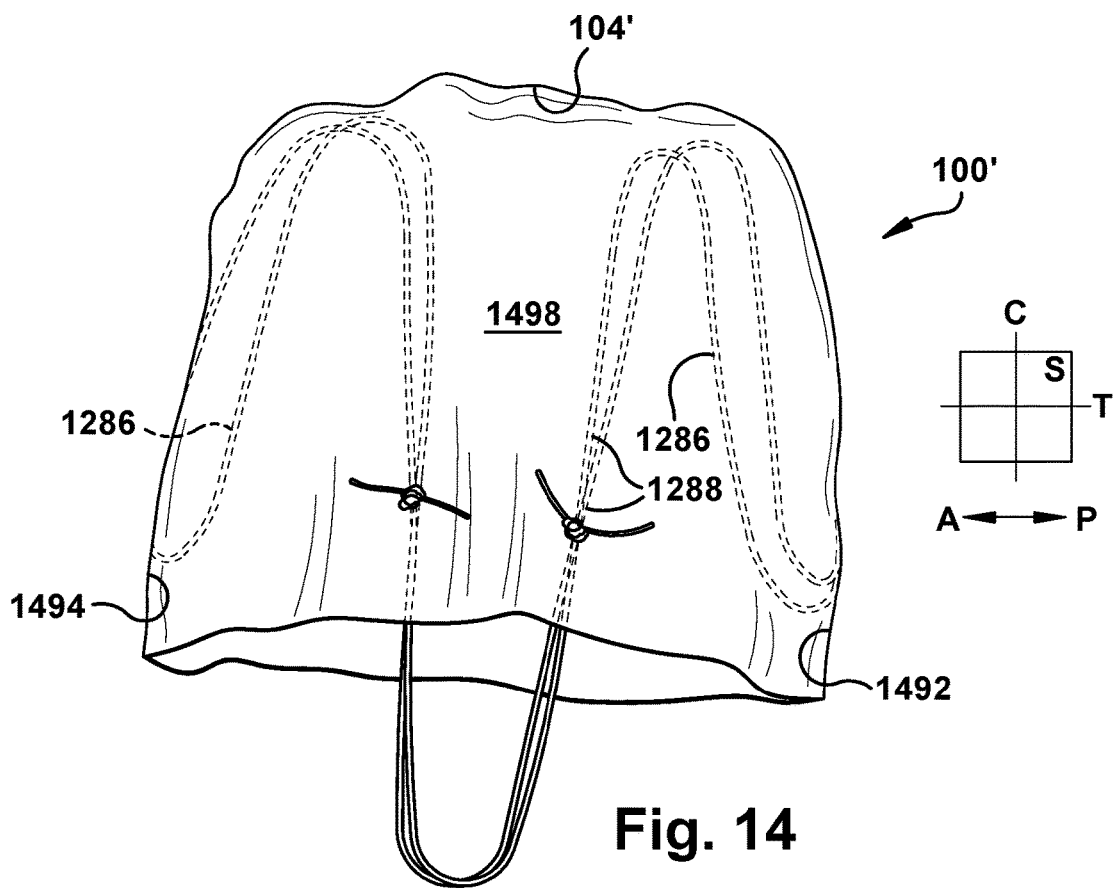
FIG. 14 is a front view of the component of FIG. 12 embodied in an aspect of the present invention.
Figure 15:
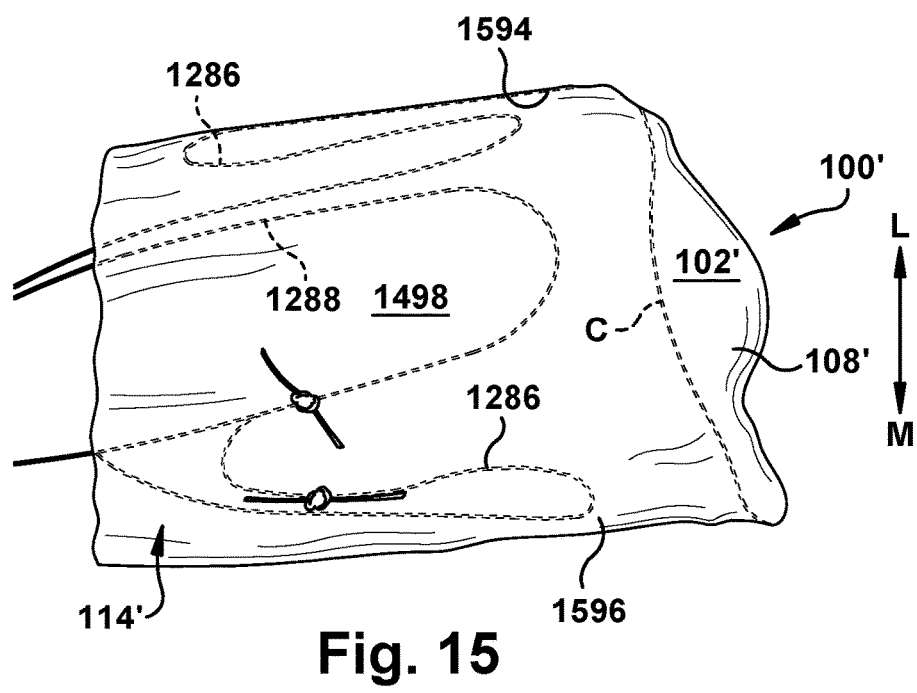
FIG. 15 is a partial side view of the aspect of FIG. 14.
Figure 16:
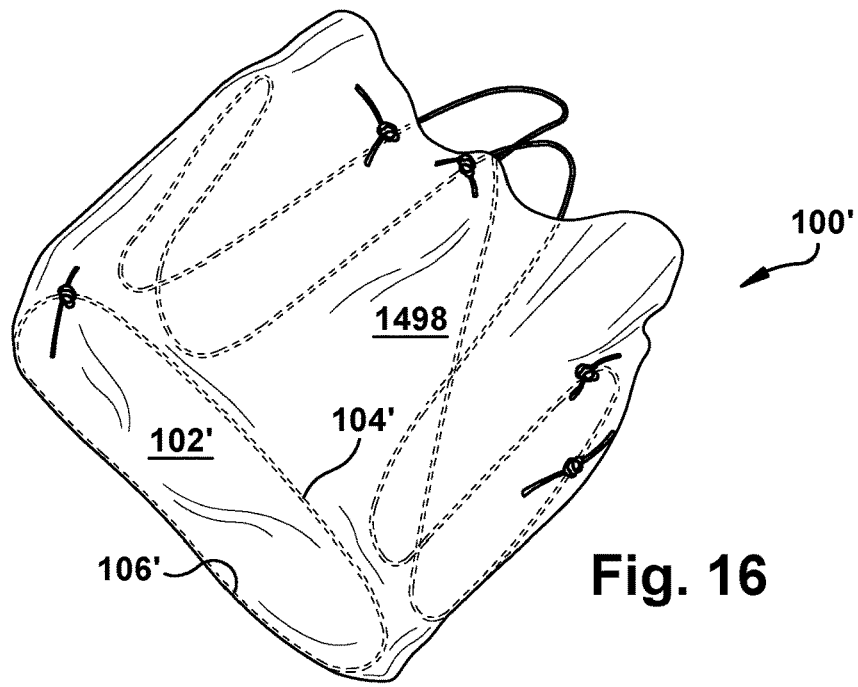
FIG. 16 is a perspective top view of the aspect of FIG. 14.

FIG. 13 is an "unrolled" or disassembled view of an embodiment of the supporting structure frame 236', including example dimensions (in millimeters and degrees) of the structures thereof. (It should be noted that, like all Figures of this application, FIG. 13 cannot be presumed to be shown to scale.) While the supporting structure frame 236' of FIGS. 12-13 includes alternating ones of two each of reduced-height struts 1286 and full-height struts 1288, it is contemplated that any desired arrangement or pattern of struts could be provided for a particular use environment. The supporting structure frame 236' structure partially shown in FIG. 13 may be made from any suitable material such as, but not limited to, 0.014" NiTinol wire. FIGS. 14-17 depict various views of an ovoid cylindrical solid device formed of a frame (similar to the frame of FIG. 13 if rolled up) having one reduced-height strut 1286 associated with each of the anteriormost and posteriormost extremities thereof (edges 1490 and 1492) and one full-height strut 1288 associated with each of the medialmost and lateralmost extremities thereof (edges 1594 and 1596, in FIG. 15). Accordingly, as can be seen in at least FIG. 14, the supporting structure frame 236' has a "saddle" or "Easter lily" type shape, which is at least partially covered by an open-bottomed cloth "cup" made of graft material. Optionally, and as shown toward the left side of FIG. 13, the medialmost one of the full-height struts may have a larger opening angle than the lateralmost one, in order to provide the desired relative radii of curvature to the lateral and medial occluding surface edges 104' and 106', as shown in FIGS. 10 and 16.

Stated differently, FIGS. 10-20 depict an implantable expandable device 100' for substantially blocking bloodflow through a false lumen 760 of a dissected aorta 762. An occluding surface 102' is oriented substantially in a transverse plane. The occluding surface 102' is bounded by a lateral occluding surface edge 104' and a medial occluding surface edge 106'. The lateral occluding surface edge 104' has a first radius of curvature which is positively curved toward the lateral direction, and the medial occluding surface edge 106' has a second radius of curvature which is positively curved toward the lateral direction, as shown in FIGS. 10-11. The second radius of curvature is larger than the first radius of curvature. The occluding surface 102' has an occluding surface body 108' located transversely between the lateral and medial occluding surface edges 104' and 106'. A majority of the lateral occluding surface edge 104' may be located in a substantially similar superior-inferior elevation (e.g., by being substantially co-located in the same transverse plane) as is a majority of the medial occluding surface edge 106'. The occluding surface 102' of the second embodiment substantially occludes a transverse cross-section of the false lumen 760 to substantially block bloodflow in the superior-inferior direction within the false lumen 760, in a substantially similar way as the bloodflow is blocked by the occluding surface 102 of the first embodiment, described above.

A supporting structure 114' is located entirely inferiorly to the occluding surface 102'. The supporting surface 114' includes a plurality of struts extending substantially in the superior-inferior direction, as shown in at least FIGS. 12-14. At least a first one of the struts is a full-height strut 1288 and spans substantially a full superior-inferior height ("H", in FIG. 13) of the device 100'. At least a second one of the struts is a reduced-height strut 1286 and spans substantially less than a full superior-inferior height H of the device 100'. For example, as shown in FIG. 13, the reduced-height struts 1286 could span approximately half of the superior-inferior height H. Optionally, the supporting structure 114' may include a plurality of full-height struts 1288 and a plurality of reduced-height struts 1286, with the full-height and reduced-height struts 1288 and 1286 being spaced apart from each other around a circumference ("C", in FIGS. 13, 15, and 18) of the supporting structure 114'. The full-height and reduced-height struts 1288 and 1286 may be alternatingly placed around the circumference C of the supporting structure 114'—that is, as one travels around the circumference C of the supporting, every other strut encountered will be a full-height strut 1288, with sequential full-height struts 1288 having a reduced-height strut 1286 interposed therebetween.

As shown in FIGS. 14-20, the supporting structure 114' of the device 100' may be at least partially covered by a flexible shroud 1498 extending around a circumference C of the supporting structure 114'. The flexible shroud 1498 may be attached to an outside (e.g., FIGS. 14-19) and/or an inside (e.g., FIG. 20) of the supporting structure 114', in any desired manner. For example, the supporting structure 114' could be directly or indirectly attached to the flexible shroud 1498 via one or more fasteners such as, but not limited to, clips, sutures, adhesives, barbs, staples, sleeves, wires, or the like. As shown in FIGS. 14-19, the supporting structure 114' may be, for example, attached via fasteners (shown in the Figures as sutures) to an inner surface of the flexible shroud 1498.

The flexible shroud 1498 may be an extension of the occluding surface 102', continuously inferiorly extending from the lateral and medial occluding surface edges 104' and 106' in a "waterfall" type continuous manner. This extension relationship may be established between the occluding surface 102' and the flexible shroud 1498 in any desired manner; in FIGS. 14-18, the occluding surface 102' and the flexible shroud 1498 are integrally formed in a unitary manner from a single piece of material which is folded, tucked, shaped, and attached together (here, sewn together) into the shroud/occluding surface structure shown in these Figures.

Figure 19:
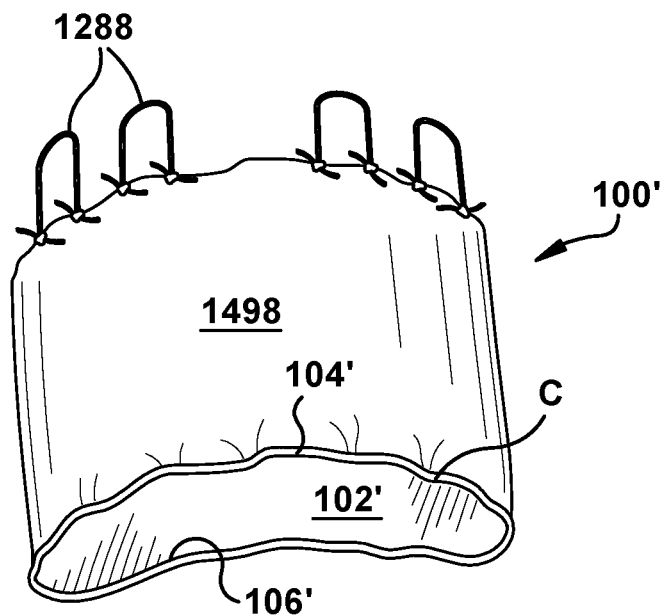
FIG. 19 is a perspective top view of the aspect of FIG. 10.
Figure 20:
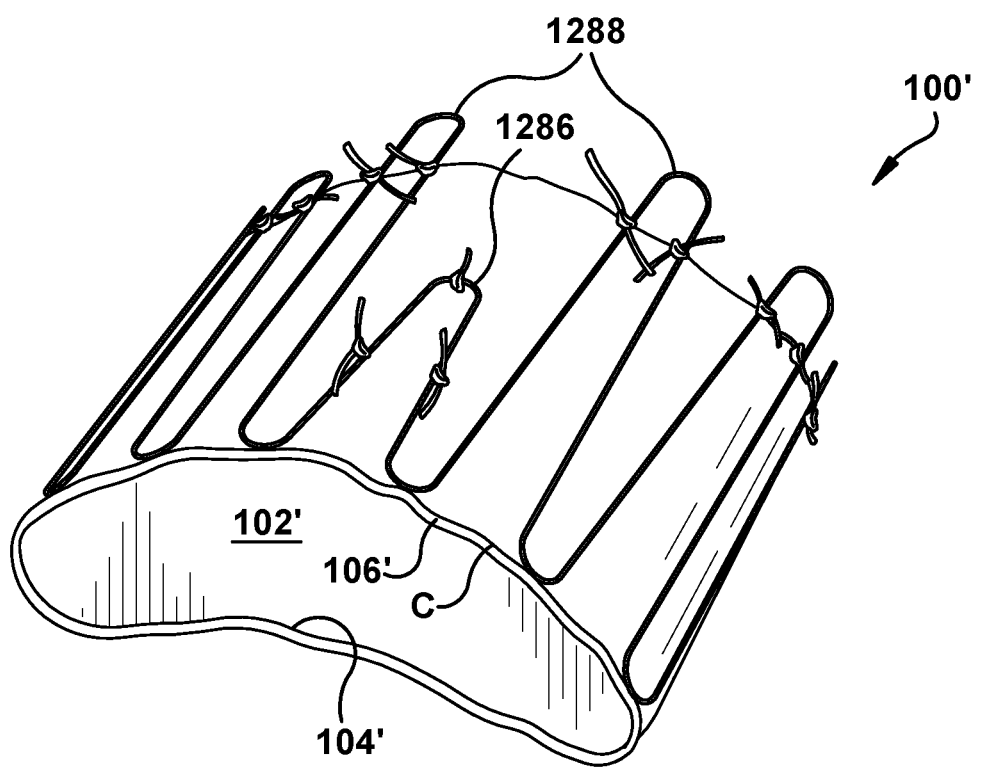
FIG. 20 is a perspective top view of an alternate configuration of the aspect of FIG. 10.

Alternatively, and as shown in FIGS. 19-20, the occluding surface 102' may be separately provided and sewn, or otherwise attached, to a flexible shroud 1498. In FIGS. 19-20, a two-piece construct, corresponding to the shape shown in FIGS. 10-11, is created through attachment of an occluding surface 102' to a separate flexible shroud 1498 via a stitched interface around circumference C of the supporting structure 114'.

Regardless of the precise nature and construction of the components of the device 100', it is contemplated that the occluding surface 102' and the flexible shroud 1498 may be formed in any desired manner, and from any desired material, though the material will likely be at least partially flexible for most use environments of the device 100'. For example, the occluding surface 102' in the flexible shroud 1498 may be formed from graft material, and are optionally collectively and integrally formed from graft material (as shown in FIGS. 14-18). It is also contemplated that at least a portion of the occluding surface 102' and/or the flexible shroud 1498 could include a surface treatment configured to promote thrombosis, as previously discussed.

Figure 17:
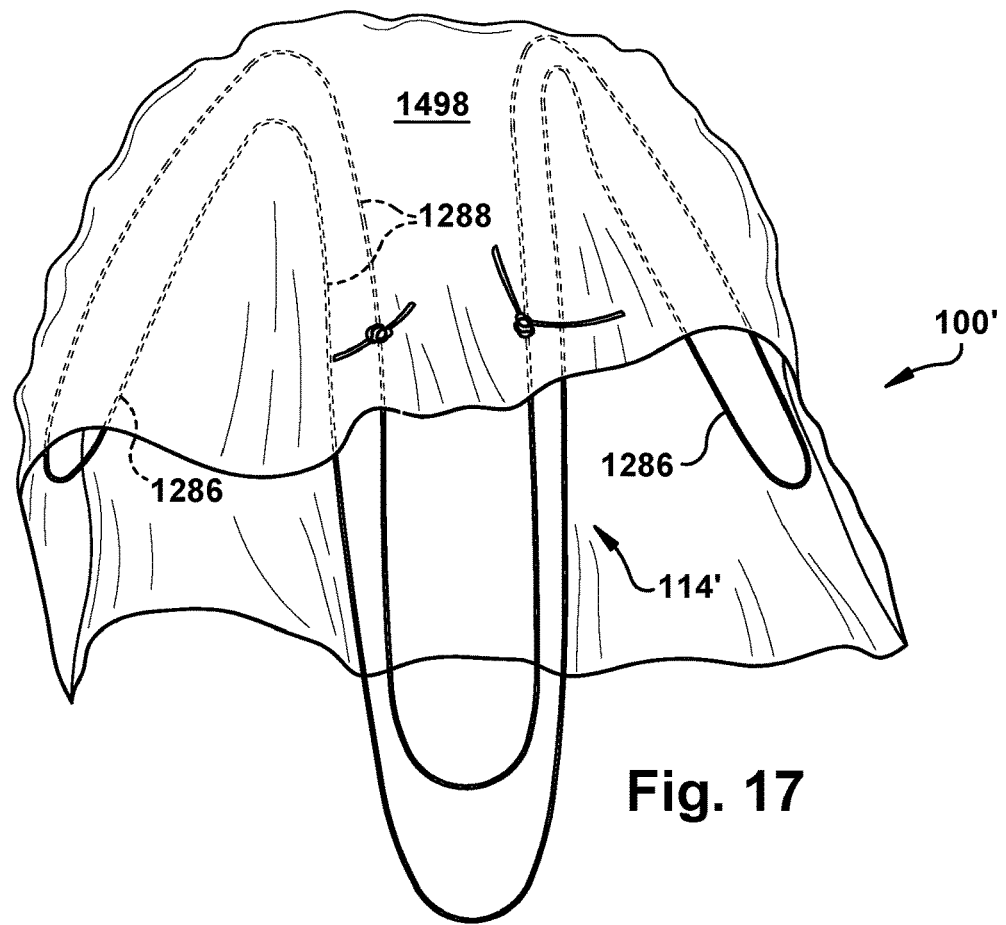
FIG. 17 is a perspective bottom view of the aspect of FIG. 14.
Figure 18:
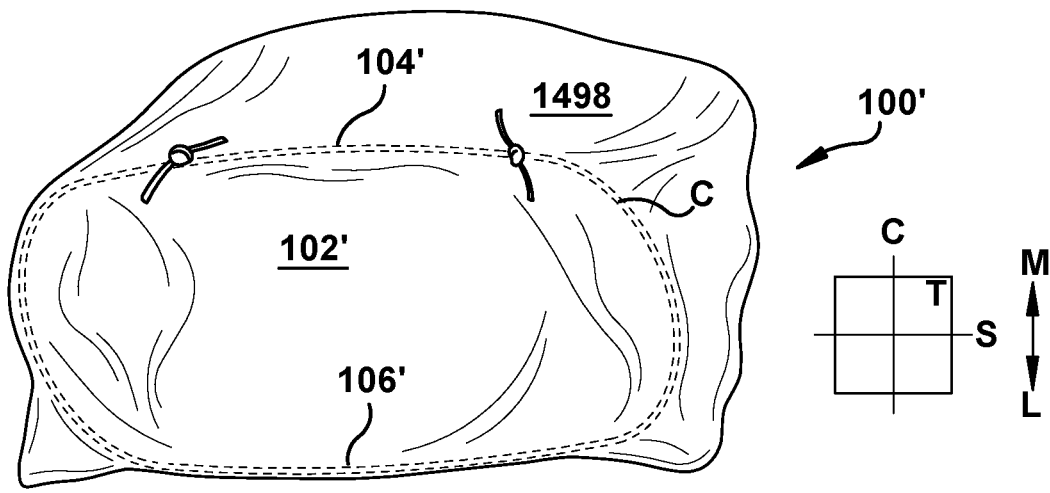
FIG. 18 is a top view of the aspect of FIG. 14.

An inferior side of the flexible shroud 1498 may be open to ambient space, such as the open "bottom" side of the device 100', particularly visible in FIG. 17. Alternatively, though not shown, the flexible shroud 1498 could be at least partially filled, or otherwise occluded, at the inferior side thereof, as desired.

The device 100' according to the second embodiment will be installed/deployed substantially similarly to that of the first embodiment, with the device 100', in the collapsed condition, being passed through a vasculature of the patient and placed substantially in the desired deployment position within the false lumen 760. The device 100' is then expanded within the false lumen 760 and maintained in the desired deployment position in the expanded condition, where the device 100' substantially occludes the transverse cross-section of the false lumen 760 with the occluding surface 102' to substantially block bloodflow in the superior-inferior direction within the false lumen 760. The device 100' could be deployed in an orientation within the false lumen 760 of the descending aorta so that the occluding surface 102' is proximal, and the open "bottom" side of the device 100' would be placed more distal, for some use environments—thus, the flexible shroud 1498 may at least partially fill with blood within the false lumen 760. In other use environments, the occluding surface 102' would be distal and the open "bottom" side of the device 100' would be more proximal, as desired by one of ordinary skill in the art.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

I claim:

1. An implantable expandable device for substantially blocking bloodflow through a false lumen of a dissected aorta of a patient, a body of the patient defining transverse, coronal, sagittal, lateral, medial, anterior, posterior, inferior, and superior directions, the device comprising:
   an occluding surface oriented substantially in a transverse plane, the occluding surface being bounded by a lateral occluding surface edge and a medial occluding surface edge, the lateral occluding surface edge having a first radius of curvature which is positively curved toward the lateral direction, and the medial occluding surface edge having a second radius of curvature which is positively curved toward the lateral direction, the second radius of curvature being larger than the first radius of curvature, the occluding surface having an occluding surface body located transversely between the lateral and medial occluding surface edges; and
   a supporting structure located entirely inferiorly to the occluding surface, the supporting structure including a plurality of struts extending substantially in the superior-inferior direction, at least a first one of the struts being a full-height strut and spanning substantially a full superior-inferior height of the device, and at least a second one of the struts being a reduced-height strut and spanning substantially less than a full superior-inferior height of the device, the supporting structure tapering inward in at least one of the anterior to posterior, posterior to anterior, medial to lateral, and lateral to medial directions over an inferiorly extending direction from the occluding surface;
   wherein the occluding surface substantially occludes a transverse cross-section of the false lumen to substantially block bloodflow in the superior-inferior direction within the false lumen.

2. The device of claim 1, wherein the supporting structure includes a plurality of full-height struts and a plurality of reduced-height struts, with the full-height and reduced-height struts being spaced apart from each other around a circumference of the supporting structure.

3. The device of claim 2, wherein the full-height and reduced-height struts are alternatingly placed around the circumference of the supporting structure.

4. The device of claim 1, wherein the supporting structure is at least partially covered by a flexible shroud extending around a circumference of the supporting structure.

5. The device of claim 4, wherein the flexible shroud is an extension, continuously inferiorly extending from the lateral and medial occluding surface edges, of the occluding surface.

6. The device of claim 5, wherein the occluding surface and flexible shroud are collectively and integrally formed from graft material.

7. The device of claim 4, wherein the supporting structure is attached via fasteners to an inner surface of the flexible shroud.

8. The device of claim 4, wherein at least a portion of the flexible shroud includes a surface treatment configured to promote thrombosis.

9. The device of claim 1, wherein an inferior side of the flexible shroud is open to ambient space.

10. The device of claim 1, wherein a majority of the lateral occluding surface edge is located in a substantially similar superior-inferior elevation as is a majority of the medial occluding surface edge.

11. The device of claim 1, wherein at least a portion of the occluding surface includes a surface treatment configured to promote thrombosis.

12. A method of substantially blocking bloodflow through a false lumen of a dissected aorta of a patient, a body of the patient defining transverse, coronal, sagittal, lateral, medial, anterior, posterior, inferior, and superior directions, the method comprising:
   providing an implantable expandable device for substantially blocking bloodflow through the false lumen, the device being configured for selective movement between collapsed and expanded device conditions, the device including
      an occluding surface oriented substantially in a transverse plane, the occluding surface being bounded by a lateral occluding surface edge and a medial occluding surface edge, the lateral occluding surface edge having a first radius of curvature which is positively curved toward the lateral direction, and the medial occluding surface edge having a second radius of curvature which is positively curved toward the lateral direction, the second radius of curvature being larger than the first radius of curvature, the occluding surface having an occluding surface body located transversely between the lateral and medial occluding surface edges, and a supporting structure located entirely inferiorly to the occluding surface, the supporting structure including a plurality of struts extending substantially in the superior-inferior direction, at least a first one of the struts being a full-height strut and spanning substantially a full superior-inferior height of the device, and at least a second one of the struts being a reduced-height strut and spanning substantially less than a full superior-inferior height of the device, the supporting structure tapering inward in at least one of the anterior to posterior, posterior to anterior, medial to lateral, and lateral to medial directions over an inferiorly extending direction from the occluding surface, wherein the occluding surface substantially occludes a transverse cross-section of the false lumen to substantially block bloodflow in the superior-inferior direction within the false lumen;

passing the device, in the collapsed condition, through a vasculature of the patient;

placing the device, in the collapsed condition, substantially in the desired deployment position within the false lumen;

expanding the device within the false lumen;

maintaining the device in the desired deployment position in the expanded condition; and when the device is in the expanded condition within the false lumen, substantially occluding a transverse cross-section of the false lumen with the occluding surface to substantially block bloodflow in the superior-inferior direction within the false lumen.

13. The method of claim 12, wherein expanding the device, within the false lumen, in the desired deployment position into the expanded condition includes positioning and maintaining a majority of the lateral occluding surface edge in a substantially similar superior-inferior elevation to a majority of the medial occluding surface edge.

14. The method of claim 12, wherein providing the device includes:

providing the supporting structure with a plurality of full-height struts and a plurality of reduced-height struts; and spacing the full-height struts and reduced-height struts apart from each other around a circumference of the supporting structure.

15. The method of claim 14, wherein providing the supporting structure with a plurality of full-height struts and a plurality of reduced-height struts includes placing the full-height and reduced-height struts alternatingly around the circumference of the supporting structure.

16. The method of claim 12, wherein providing the device includes at least partially covering the supporting structure with a flexible shroud extending around a circumference of the supporting structure.

17. The method of claim 16, wherein at least partially covering the supporting structure with a flexible shroud includes providing the flexible shroud as an extension, continuously inferiorly extending from the lateral and medial occluding surface edges, of the occluding surface.

18. The method of claim 17, wherein providing the flexible shroud as an extension of the occluding surface includes collectively and integrally forming the occluding surface and flexible shroud from graft material.

19. The method of claim 16, wherein at least partially covering the supporting structure with a flexible shroud includes attaching the supporting structure via fasteners to an inner surface of the flexible shroud.

20. The method of claim 16, including, with a surface treatment of at least a portion of the flexible shroud, promoting thrombosis within the false lumen.

21. The method of claim 12, including, with a surface treatment of at least a portion of the occluding surface, promoting thrombosis within the false lumen.

* * * * *